(12) United States Patent
Raniere (10) Patent No.: US 9,421,447 B2
(45) Date of Patent: *Aug. 23, 2016

(54) METHOD AND APPARATUS FOR IMPROVING PERFORMANCE

(75) Inventor: Keith A. Raniere, Clifton Park, NY (US)

(73) Assignee: FIRST PRINCIPLES, INC., Albany, NY (US)

( * ) Notice: Subject to any disclaimer, the term of this patent is extended or adjusted under 35 U.S.C. 154(b) by 127 days.

This patent is subject to a terminal disclaimer.

(21) Appl. No.: 11/457,006

(22) Filed: Jul. 12, 2006

(65) Prior Publication Data

US 2006/0247096 A1 Nov. 2, 2006

Related U.S. Application Data

(62) Division of application No. 10/631,279, filed on Jul. 31, 2003.

(51) Int. Cl.
| | |
|---|---|
| *A63B 71/06* | (2006.01) |
| *A63B 24/00* | (2006.01) |
| *A63B 23/18* | (2006.01) |
| *A61B 5/22* | (2006.01) |
| *A63B 21/06* | (2006.01) |
| *A63B 22/02* | (2006.01) |
| *G09B 19/00* | (2006.01) |

(52) U.S. Cl.
CPC ....... *A63B 71/0619* (2013.01); *A63B 24/0062* (2013.01); *A61B 5/222* (2013.01); *A63B 21/06* (2013.01); *A63B 22/02* (2013.01); *A63B 23/18* (2013.01); *A63B 2024/0068* (2013.01); *A63B 2024/0078* (2013.01); *A63B 2071/068* (2013.01); *A63B 2220/30* (2013.01); *A63B 2220/803* (2013.01); *A63B 2225/20* (2013.01); *A63B 2225/50* (2013.01); *A63B 2230/00* (2013.01); *A63B 2230/06* (2013.01); *A63B 2230/30* (2013.01); *G09B 19/0038* (2013.01)

(58) Field of Classification Search
USPC ......... 482/7, 5, 900, 8, 1; 434/247, 254, 255
See application file for complete search history.

(56) References Cited

U.S. PATENT DOCUMENTS

| | | | |
|---|---|---|---|
| 4,408,183 A | 10/1983 | Wills | |
| 4,463,764 A | 8/1984 | Anderson et al. | |

(Continued)

FOREIGN PATENT DOCUMENTS

| | | |
|---|---|---|
| AU | 2004262334 | 5/2011 |
| CN | 1176833 A | 3/1998 |

(Continued)

OTHER PUBLICATIONS

John Straton et al. "Cardiovascular responses to exercise. Effects of aging and exercise training in healthy men." Jan. 4, 19941 Journals of American Heart Association. Circulation, vol. 89, p. 1648-1655. Retrieved on Mar. 28, 2007. <Retrieved from the internet http:llw-ww.circ.ahajournals.orglcgilreprint1891411648 >.*

(Continued)

*Primary Examiner* — Robert J Utama
(74) *Attorney, Agent, or Firm* — Schmeiser, Olsen & Watts, LLP (57) ABSTRACT

The present invention relates generally to a training method and apparatus for improving performance.

11 Claims, 6 Drawing Sheets

(56) References Cited

U.S. PATENT DOCUMENTS

| | | | | |
|---|---|---|---|---|
| 4,542,897 | A | * | 9/1985 | Melton et al. ............... 463/7 |
| 4,828,257 | A | | 5/1989 | Dyer et al. |
| 5,001,632 | A | * | 3/1991 | Hall-Tipping ............... 463/7 |
| 5,308,300 | A | | 5/1994 | Chino et al. |
| 5,410,472 | A | | 4/1995 | Anderson |
| 5,941,837 | A | | 8/1999 | Amano et al. |
| 6,592,502 | B1 | | 7/2003 | Phillips |
| 6,648,827 | B2 | | 11/2003 | Heikkila et al. |
| 6,702,720 | B2 | * | 3/2004 | Dardik ............... 482/13 |
| 6,736,759 | B1 | | 5/2004 | Stubbs et al. |
| 6,795,294 | B2 | | 9/2004 | Kuroda et al. |
| 6,939,881 | B2 | | 9/2005 | Pipers |
| 6,997,852 | B2 | * | 2/2006 | Watterson et al. ............... 482/1 |
| 7,054,678 | B2 | | 5/2006 | Dardik et al. |
| 2003/0006903 | A1 | | 1/2003 | Naegely et al. |
| 2004/0152054 | A1 | | 8/2004 | Gleissner et al. |
| 2006/0293617 | A1 | | 12/2006 | Einav et al. |

FOREIGN PATENT DOCUMENTS

| | | |
|---|---|---|
| CN | 1370502 A | 9/2002 |
| CN | 1853211 A | 10/2006 |
| IN | 262515 | 7/2004 |
| JP | 2003111877 A | 4/2003 |
| JP | 5067784 B2 | 11/2012 |
| JP | 5701823 B2 | 4/2015 |
| MX | PA06001301 A | 5/2006 |
| WO | 9620640 A1 | 7/1996 |

OTHER PUBLICATIONS

Kindermann et al. "The Significance of an Anerobic-anaerobic Transition for the Determiniation of Work Load Intensities During Endurance Training." Eur J. Appl. Physiol 42, p. 25-34, 1979.*

Yoshida et al. "Endurance Training Regimen Based Upon Arterial Blood Lactate: Effects on Anaerobic Threshold" Eur J Appl Physiol 1982 p. 223-230.*

Half Marathon Training, Running and Racing . . . Part Two, Anaerobic Threshold Training. [online]. 3 pages. [retrieved on Aug. 17, 2000]. Retrieved from the Internet:<URL: http://home.sprynet.com/~holtrun/halfmara.htm>.

Balbach, Lisa. What is Aerobic Exercise and Why Should I do it? [online]. 2 pages. [retrieved on Aug. 16, 2000]. Retrieved from the Internet:< URL: http://k2.kirtland.cc.mi.us/—balbach1/aeroprin.htm>.

Higdon, Hal. Hal Higdon's Marathon Training Guide—Novice Program. [online]. 2 pages. [retrieved on Aug. 17, 2000]. Retrieved from the Internet:< URL: http://www.halhigdon.com/marathon/nprogram.html>.

Higdon, Hal. Hal Higdon's Marathon Training Guide—Advanced Program. [online]2 pages. [retrieved on Aug. 17, 2000]. Retrieved from the Internet:< URL: http://www.halhigdon.com/marathon/eprogram.html>.

Tucker, James A., DC,CCN. Aerobic Exercise. [online]. 3 pages. [retrieved on Aug. 16, 2000]. Retrieved from the Internet:< URL: http://www.jkfa.com/alpub/aerobics.htm>.

Star Trac Model 4500 Treadmill. [online]. 2 pages. (Product information page) iTreadmills.comTM [retrieved on Nov. 8, 2000]. Retrieved from the Internet:< URL: http://www.itreadmills.com/startrac/tr4500_treadmill.htm>.

Office Action (Mail Date Jun. 10, 2010) for U.S. Appl. No. 10/631,279, filed Jul. 31, 2003; Confirmation No. 3766.

Office Action (Mail Date Jul. 26, 2012) for U.S. Appl. No. 11/456,976, filed Jul. 12, 2006; Confirmation No. 6443.

Should I train to Failure, http://www.streetdirectory.com/travel_guide/43060/fitness/should_i_train_to_failure.html>: dated Nov. 19, 2009, 3 pages.

Pierson, Vicky. "Understanding Your Training Heart Rate" Retrieved at Jun. 21, 2997 ,Retrieved from: http://web.archive.org/web/19970621122415/http://primusweb.com/fitnespartner/library/activity/thr.htm>; 5 pages.

Hervert, Jack "PED—Chapter 14 Notes" [Retrieved Jul. 29, 2003] Retrieved from the Internet. <URL: http://web.archive.org/web/20030729113130'http://waukesha.uwc.edu/ped/jhervert/ped291/chap14.html>.

Stevens, Kathy "Interval Training: alternating periods of high- and low-intensity exercise for maximum benefit—includes continuing education test." American Fitness. Jul.-Aug. 1997 [Retrieved Apr. 26, 2011] Retrieved from the internet < URL: http://findarticles.com/p/artioles/mi_m0675/is_n4_v15/ai_19575697 >.

"Exercise Safety" [Retrieved: Feb. 10, 2001] Retrieved from the Internet. < URL: http://webarchive.org/web/20010210021034/http://www.lifeclinic.com/focus/weight/safety_ex_asp>.

Office Action (Mail Date Jan. 4, 2011) for U.S. Appl. No. 11/456,976, filed Jul. 12, 2006.

Application No. PCT/US2004/24147, International Search Report and the Written Opinion of the International Searching Authority, or the Declaration dated Jan. 5, 2006. 10 pages.

Office Action (Mail Date Apr. 26, 2011) for U.S. Appl. No. 11/456,976, filed Jul. 12, 2006.

Non-Final Office Action for U.S. Appl. No. 10/631,279, filed Jul. 31, 2003), mailed on Aug. 7, 2015.

Office Action for U.S. Appl. No. 11/457,006, filed Jul. 12, 2006), mailed on Aug. 20, 2012.

Canadian Office Action for application No. 2,534,434, dated Oct. 18, 2008.

Canadian Office Action for application No. 2,534,434, Office Action dated Sep. 8, 2009.

Canadian Office Action for application No. 2,534,434, Office Action dated Aug. 10, 2010.

Canadian Office Action for application No. 2,534,434, Office Action dated Jun. 27, 2011.

Canadian Office Action for application No. 2,534,434, Office Action dated Jul. 3, 2012.

Canadian Office Action for application No. 2,534,434, Office Action dated May 15, 2013.

Canadian Office Action for application No. 2,534,434, Office Action dated Mar. 5, 2014.

Canadian Office Action for application No. 2,534,434, Office Action dated Mar. 5, 2015.

International Search Report and Written Opion for PCT Appln. No. PCT/US04/24147, mailed on Jan. 5, 2006; 10 pages.

International Preliminary Report on Patentability for PCT Appln. No. PCT/US04/21417, mailed on Jun. 12, 2006; 5 pages.

Non-Final Office Action for U.S. Appl. No. 11/456,976, filed Jul. 12, 2006), mailed on Sep. 17, 2015.

Office Action (Mail Date Apr. 4, 2006) for U.S. Appl. No. 10/631,279, filed Jul. 31, 2003.

Office Action (Mail Date Dec. 14, 2006) for U.S. Appl. No. 10/631,279, filed Jul. 31, 2003.

Office Action (Mail Date Apr. 25, 2007) for U.S. Appl. No. 10/631,279, filed Jul. 31, 2003.

Office Action (Mail Date Sep. 21, 2007) for U.S. Appl. No. 10/631,279, filed Jul. 31, 2003.

Office Action (Mail Date Mar. 26, 2008) for U.S. Appl. No. 10/631,279, filed Jul. 31, 2003.

Office Action (Mail Date Sep. 30, 2008) for U.S. Appl. No. 10/631,279, filed Jul. 31, 2003.

Office Action (Mail Date Apr. 20, 2009) for U.S. Appl. No. 10/631,279, filed Jul. 31, 2003.

Office Action (Mail Date Nov. 24, 2009) for U.S. Appl. No. 10/631,279, filed Jul. 31, 2003.

Office Action (Mail Date Nov. 24, 2010) for U.S. Appl. No. 10/631,279, filed Jul. 31, 2003.

Office Action (Mail Date Apr. 26, 2011) for U.S. Appl. No. 10/631,279, filed Jul. 31, 2003.

Office Action (Mail Date May 23, 2008) for U.S. Appl. No. 11/456,976, filed Jul. 12, 2006.

(56) References Cited

OTHER PUBLICATIONS

Office Action (Mail Date Nov. 26, 2008) for U.S. Appl. No. 11/456,976, filed Jul. 12, 2006.

Office Action (Mail Date Jun. 24, 2009) for U.S. Appl. No. 11/456,976, filed Jul. 12, 2006.

Office Action (Mail Date Jan. 7, 2010) for U.S. Appl. No. 11/456,976, filed Jul. 12, 2006.

* cited by examiner

METHOD AND APPARATUS FOR IMPROVING PERFORMANCE

This application is a divisional of Ser. No. 10/631,279; filed on Jul. 31, 2003.

FIELD OF THE INVENTION

The present invention relates generally to a method and apparatus for improving performance.

BACKGROUND OF THE INVENTION

Training methods, or programs, are used to improve performance in numerous endeavors, be they individual athletic endeavors with equipment (e.g., throwing, weight lifting, etc.) or individual athletic endeavors without equipment (e.g., running, jumping, swimming, etc.), team athletic endeavors (e.g., baseball, soccer, etc.), mental endeavors (e.g., IQ testing, memory recall, mental calculations, trivia games, etc.), or emotional endeavors (e.g., acting, presenting, competition, etc.). Typically, the individual trains by performing for a fixed distance or a fixed quantity. For example, a swimmer may swim for 100 meters or a runner may run for a mile or a weightlifter may bench press 250 pounds or a mathematician may calculate 100 sums or a presenter maintains a peak emotional state in the face of adversity for a fixed time. An individual repeats the fixed distances or quantities and attempts to improve the time required to travel fixed distances or complete the fixed quantity of mental calculations or achieve the emotional state during the physical and/or mental activities.

SUMMARY OF THE INVENTION

The present invention provides a method of training based upon continuous variables (e.g., distance, time duration, weight gradient, etc.) rather than upon discrete variables (e.g., a fixed mark, fixed repetitions, etc.). The individual is trained to produce a level of performance (e.g., energy, thrust, speed, mental tasks, etc.) for a length of the continuous variable (which may actually be discrete, but then is unfixed), such as time, which is constantly challenged. Gradually, the individual is able to produce the same level of performance over improved periods of the continuous variable, say time, for activities such as running and swimming or produce the same level of performance with shorter periods of rest between activities such as repetitions of lifting weight or produce the same activity in a shorter time like calculating a quantity of mathematical sums. Ultimately, the principle applied with this new method of improving performance, which is deemed "Raniere's Maximal Efficiency Principle™" or "Raniere's Law™", is where the characteristic or variable to be trained is, optimally, continuously challenged. For example, if your performance improvement goal is for runners to run longer distances, then you continuously challenge distance (e.g., try to beat the last, longest distance ran). Similarly, if your performance improvement goal is for greater speed, then you continuously challenge speed (e.g., as on a treadmill). Then, if your performance improvement goal is for speed over distance (i.e., speed for a length of time) then you continuously challenge the length of time at a speed (e.g., as on a treadmill).

A first general aspect of the present invention provides a method comprising:

determining if a subject is trainable with respect to the performance of a given activity;

determining a point of efficiency of a subject with respect to at least one parameter; and exerting the subject at or near the point of efficiency until a state of inefficiency with respect to the at least one parameter or exhaustion occurs.

A second general aspect of the present invention provides a method comprising:

taking a measurement relating to at least one continuous variable with respect to which a subject may remain in a state of accommodation; and training the subject so the value of the measurement of the at least one continuous variable changes.

A third general aspect of the present invention provides a method comprising:

providing a performance system;

activating the performance system;

recording at least one parameter of the performance system;

measuring the at least one parameter of a subject;

determining an at least one point of efficiency parameter by changing the at least one parameter of the performance system until the at least one parameter of the subject substantially changes beyond a given tolerance function; and training the subject at or near the point of efficiency so the duration the subject can maintain the point of efficiency changes.

A fourth general aspect of the present invention provides an apparatus comprising:

a performance system;

at least one sensor for measuring at least one parameter of a subject being trained or measured by the performance system; and a control system for controlling the at least one parameter of the performance system and for acquiring the at least one parameter data from the at least one sensor.

The foregoing and other features and advantages of the invention will be apparent from the following more particular descriptions of preferred embodiments of the invention.

BRIEF DESCRIPTION OF THE DRAWINGS

The features of the present invention will best be understood from a detailed description of specific embodiments of the invention selected for the purposes of illustration and shown in the accompanying drawings in which.

DETAILED DESCRIPTION OF THE INVENTION

Although certain specific embodiments of the present invention will be shown and described in detail, it should be understood that generalizations and various changes and modifications may be made without departing from the scope of the appended claims. The scope of the present invention will in no way be limited to the number of constituting components, the materials thereof, the shapes thereof, the relative arrangement thereof, etc. Some features of the present invention are illustrated in detail in the accompanying drawings, wherein like reference numerals refer to like elements throughout the drawings. Although the drawings are intended to illustrate an embodiment of the present invention, the drawings are not necessarily drawn to scale.

The following are definitions that pertain to the subject invention:

Computer: Any device that directly or indirectly performs arithmetic operations and/or comparisons on numbers;

Variable: Any measurable quantity, quality, or property that hypothetically, or actually, can change over time;

Subject: Anything that has at least one measurable quantity, quality, or property;

Characteristic: A measurable quantity, quality, or property associated with a specific subject;

Parameter: Any characteristic used as a reference;

Performance: An effect measurement taken on a subject under specific cause conditions;

Activity: Anything from which you can derive performance;

Training: Stimuli used to affect performance; and

Trainable: Affected by training.

Figure 6:
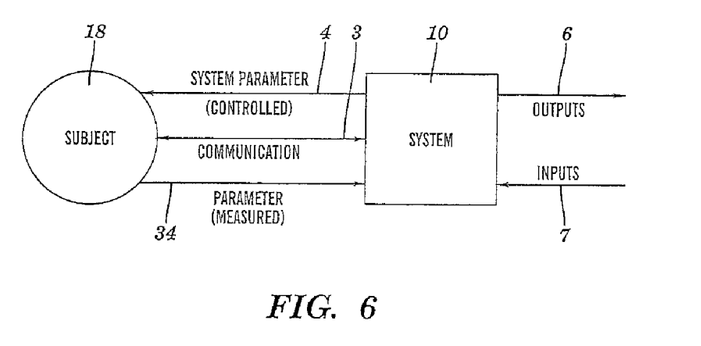

FIG. 6 illustrates a general diagram outlining the overall system that both the method and apparatus of the present invention employ. A subject 18 interacts with a system 10. The system 10 has been termed variously a training system, measuring system, or performance system. There is an interaction, or communication 3, between the subject 18 and the training system 10. The subject 18, sends to the training system 10, at least one parameter 34. The at least one parameter 34 is measured. In return, the training system 10, returns to the subject 18 a system parameter 4. The system parameter 4 is controlled. The training system 10 has both inputs 7, and outputs 6. The subject 18 needs only to be any trainable entity. An example of a trainable subject 18 is an entity that both responds to or measures in some way an external environmental effect on the entity; and, then the subject 18 has some capability of retaining memory of the cumulation of these external environmental effects. Thus, the subject 18 may be an individual human, a team or group of humans such as a running team, an animal, a group of animals, a cellular automata, a group of cellular automata, a virus programs, microorganism cultures, microbes, plants, a piece of material, a computer program and data, etc.

Figure 1:
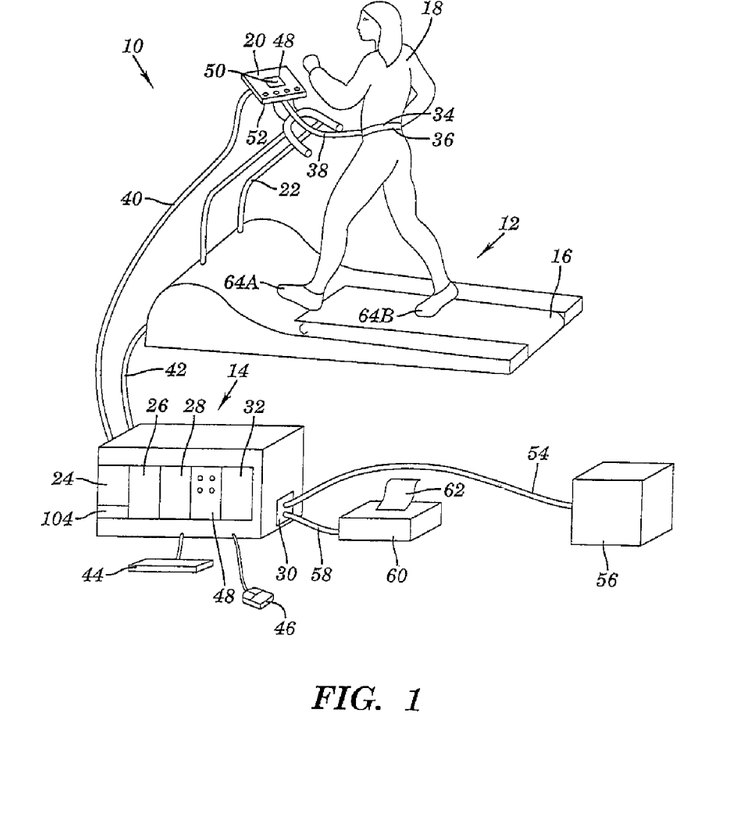
FIG. 1 illustrates a perspective view of a specific athletic (running) performance system, within the scope of the present invention.

FIG. 1 illustrates a perspective view of one specific, performance system 10 of the present invention, in this case, being utilized for runners. The performance system 10 includes a treadmill apparatus 12 and a control system 14. Optionally, the performance system 10 may be, inter alia, a stair stepping machine, bicycle, stationary bicycle, swimming pool, weightlifting apparatuses, other aerobic exercise devices, or emotional or mental exercise devices such as computer learning system, emotion trigger system, mental performance system, and biofeedback machine. The treadmill apparatus includes a belt 16 that a subject 18 may run on. The treadmill apparatus 12 may also include an interface device 20 mounted on a support 22 of the treadmill apparatus 12. The control system 14 may include, inter alia, a computer 24, a data acquisition system 26, a memory device 28, a display device 32, and an output port 30. At least one physical, emotional, or mental parameter 34 of the subject 18 is gathered by at least one sensor 36. The at least one physical, emotional, or mental parameter 34 may include any suitable measurement (e.g., running turnover rate, stride length, stride strike force, muscle contraction speed, muscle contraction profile, muscle contraction strength, body temperature, heat given off, blood pressure heart rate, heart beat strength, respiration rate, $VO_2$, perspiration rate, metabolic rate, blood flow, breathing rate, breath length, breath capacity, blood pressure, $VO_2$, ability to count backwards by 3 accurately, etc.). It is possible that all mental and emotional parameters can be considered to be measured by a physical parameter 34. To measure is to "sense" a difference with at least one of the five senses. Thereby, all emotional, thought, or other parameters 34 need to be reducible to a physical signal (e.g., signal "sensed" by one of the five senses) in order to be measured. A cable 38 connects the at least one sensor 36 to the interface device 20. A cable 40 connects the interface device 20 with the control system 14. In this embodiment, the computer 24 controls the data acquisition system 26 and the data acquisition system 26 acquires the physical parameter 34 from the at least one sensor 36 through the cable 38, through the interface device 20, and through the cable 40. The computer 24 may control the speed of the belt 16 on the treadmill apparatus 12 by sending speed commands (i.e., system parameters) through a cable 42. The computer 24 stores the physical parameter 34 and treadmill speed 66 (FIG. 2A) data in the memory device 28. An operator may send input commands to the computer 24 through any suitable input device such as a keyboard 44, a mouse 46, a keypad 48, voice recognition system (not shown), etc. The interface device 20 may include, inter alia, a display screen 50 and a plurality of buttons 52. The buttons 52 allow the subject 18 to input commands to the control system 14. The display screen 50 displays information, such as treadmill speed 66 (FIG. 2A) and physical parameters 34, to the subject 18. Additionally, the display device 32 displays information (e.g., treadmill speed 66 (FIG. 2A), physical parameters 34, charts, graphs, etc.). A cable 54 connects the output port 30 with a remote computer 56. The computer 24 of the control system 14 may send data from the memory device 28 to the remote computer 56. A cable 58 may connect the output port 30 with a printer 60. The computer 24 sends data from the memory device 28 to the printer 60. The printer 60 prints and provides a hard copy 62 of data to an operator. In lieu of any of the cables 58, the system may transmit data via wireless technology (e.g., radio frequency, infra red, acoustic, etc.).

Figures 2A, 2B:
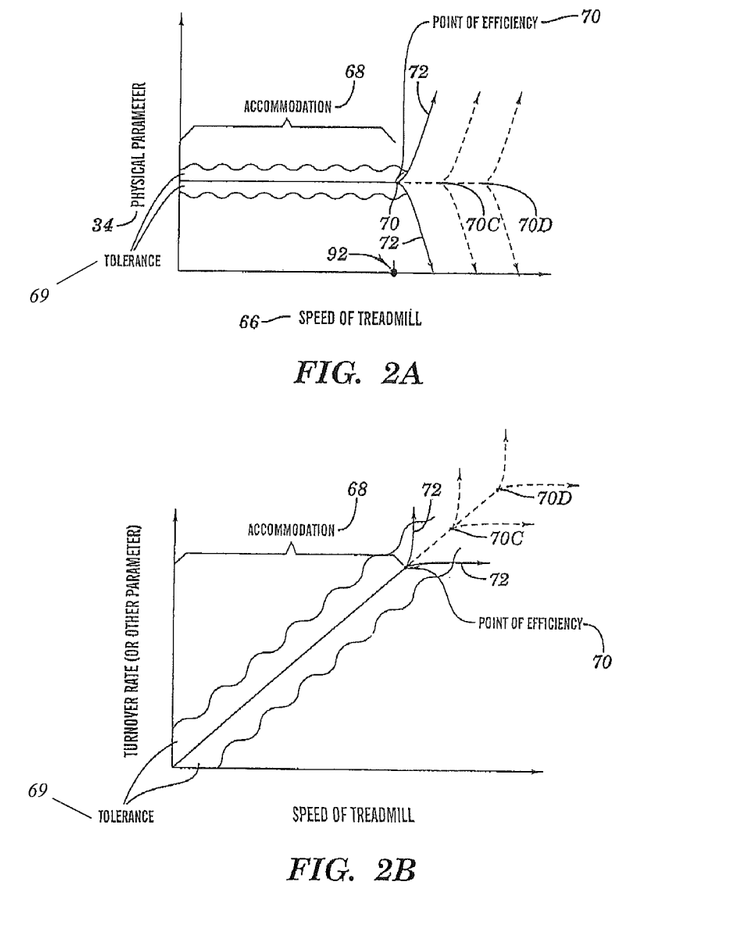
FIG. 2A illustrates an approximate graph of a physical parameter versus a speed parameter of this performance system (a treadmill), within the scope of the present invention.
FIG. 2B illustrates an approximate graph of a turnover rate versus a speed parameter of this performance system (a treadmill), within the scope of the present invention.

FIG. 2A illustrates a graph of the parameter 34 versus a speed of a treadmill 66. As mentioned above, the parameter 34, which can be a physical, emotional, or mental parameter, may include any suitable measurement of (e.g., heart rate, turnover rate, respiration rate, blood pressure, $VO_2$, etc.) of a subject 18. The turnover rate is the number of times each foot 64A, 64B of the subject 18 strikes the belt 16 of the treadmill 12 per minute. $VO_2$ is the oxygen capacity of the body of the subject 18. The graph of FIG. 2A illustrates the treadmill speed 66 being increased while a physical parameter 34, such as heart rate, is measured. In this example, as the treadmill speed 66 is increased, the heart rate varies approximately (within tolerance 69) linearly with treadmill speed in a state of accommodation 68. A state of accommodation 68, as FIG. 2A depicts, is the value at which the physical parameter 34 does not notably change in variation beyond a given functional tolerance 69. A functional tolerance 69 can be a function of time, for example, or of any one, or more, parameters. In the state of accommodation 68, the subject 18 is adjusting to the treadmill speed 66 without being overly stressed. As the treadmill speed 66 is increased, a point of efficiency 70 is reached. As the treadmill speed 66 is increased beyond the point of efficiency 70, the physical parameter 34 (e.g., heart rate, etc.) notably changes along the graph line 72. Just beyond the point of efficiency 70, the subject's 18 body and/or emotions and mind, measured through the body, no longer can accommodate additional stress and enters a state of inefficiency causing the physical parameters 34 to vary differently (e.g., more rapidly change, less rapidly change) than before. As the subject 18 trains, the point of efficiency 70 moves to higher and higher speeds as illustrated in the point of efficiencies 70C, and 70D (FIG. 2A). Thus, the point of efficiency 70 is the maximum value of, in the case of FIG. 2A, the speed of the treadmill whereby the state of accommodation is maintained.

FIG. 2B illustrates a graph comparing a parameter 34, in this case, turnover rate versus the speed of the treadmill 66. In this case, the turnover rate varies proportionally with the speed of the treadmill 66, within certain pre-determined tolerances 69. At a certain turnover rate a point of efficiency 70 is reached. Beyond the point of efficiency 70 the turnover rate is longer in the same proportion to the speed of the treadmill 66. That is the turnover rate is accelerating, or deaccelerating, compared to treadmill speed 66. As training is continued with this method, however, the point of efficiency 70 is increased to further new points of efficiency 70C, 70D.

Figure 3:
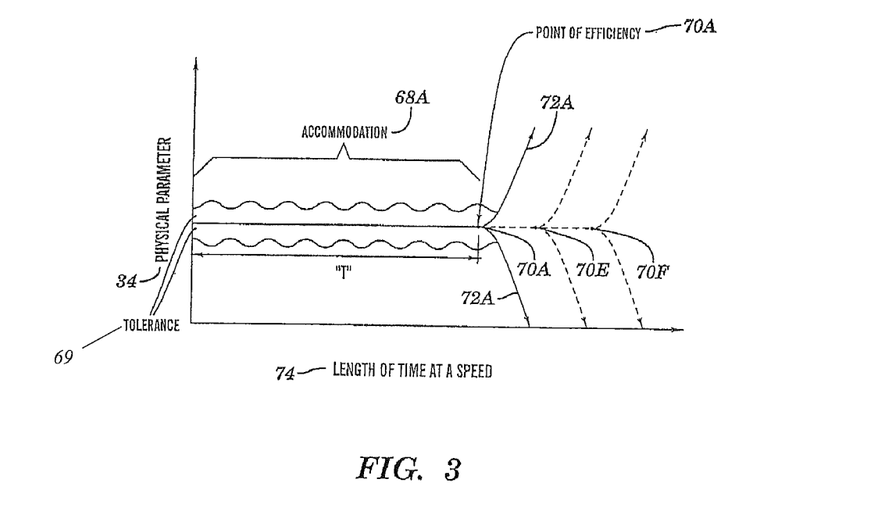
FIG. 3 illustrates a graph of a physical parameter versus a length of time at a given speed, within the scope of the present invention.

FIG. 3 illustrates a graph of the parameter 34 versus time 74. In this example, the treadmill speed 66 is maintained at a constant speed for exercising the subject 18. For a length of time denoted "T", the physical parameter 34, such as respiration rate, remains substantially linear, within a predetermined functional tolerance 69. In this state of accommodation 68A, the subject's body 18 is adjusting to the stress of exercising over the length of time 74. As time increases, a point of efficiency 70A is reached. For exercise beyond this point of efficiency 70A, the physical parameters 34 notably change along the graph line 72A. Above the point of efficiency 70A, the subject 18 no longer can accommodate additional stress and enters a state of inefficiency causing the physical parameters 34 to markedly change. The speed of the treadmill now drives the graph (i.e., point of inefficiency is driven by machine parameter variation. That is the subject 18, not being able to effectively accommodate the level of stress, becomes more reactive to the machine variance). Note that sometimes the state of inefficiency can simply be the inability to continue the activity, by setting the tolerance 69 wide enough. This is often the case with running (i.e., runner must stop) or weight training (i.e., weight can no longer be lifted). As the subject 18 trains and builds up more capacity, the point of efficiency 70A moves to, in this case, longer and longer lengths of times 74 (i.e., moves in some direction along the parameter graph) as illustrated in point of efficiencies 70E, and 70F. For the physical parameter 34 to markedly or notably change, the physical parameter 34 is no longer consistent or substantially consistent. For the physical parameter 34 to remain consistent or substantially consistent, the physical parameter 34 must stay within certain predefined, possibly parameter variation-related (functional), tolerances 69. Depending on which physical parameter 34 is being measured, the predefined tolerance 69 may vary. For example, the tolerance 69 may be set at +/−2% of the value of the physical parameter 34. Thus, in the aforementioned example, as long as the physical parameter 34 stays within +/−2% of a value, the subject 18 is still within a state of accommodation 68. These tolerances 69 can also be functions of time. In an alternative embodiment, the training may results in a shortening of the length of time that the subject is in a state of accommodation 68. For example, in weightlifting, the time the body needs to rest and recuperate between lifting sets would be shortened through successive training.

Figure 4:
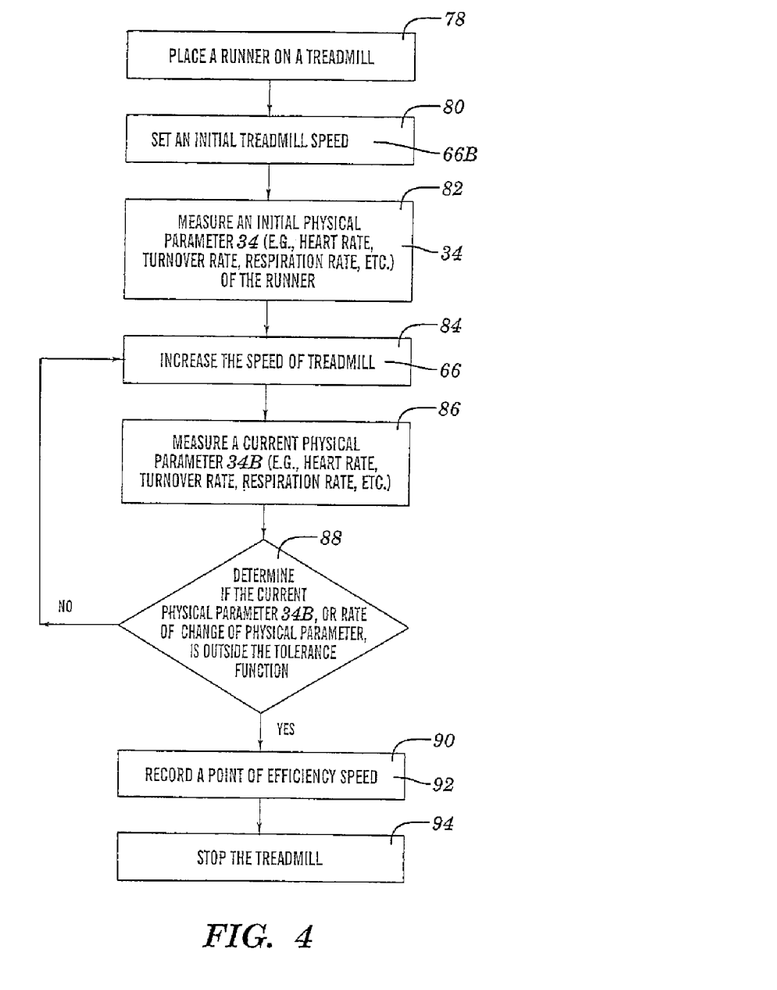
FIG. 4 illustrates a schematic view of determining a point of efficiency speed for a specific embodiment related to running, within the scope of the present invention.

FIG. 4 illustrates a schematic view of determining the point of efficiency 70 for treadmill speed 66. In step 78, the subject 18, such as a runner, is placed on the belt 16 of the treadmill apparatus 12. In step 80, an initial treadmill speed 66B is set. In step 82, a measurement is taken of an initial physical parameter 34 (e.g., heart rate, turnover rate, respiration rate, $VO_2$, etc.). In step 84, the speed of the treadmill 66 is increased. In step 86, the data acquisition system 26 of the control system 14 measures a current physical parameter 34B. In step 88, the control system 14 determines if the current physical parameter 34B is outside the tolerance function or rate of change (see diagram). The computer 24 may perform this determination. If the current physical parameter 343 is not outside the tolerance function, the method returns to step 84 where the treadmill speed 66 is further increased. If the current physical parameter 34B is outside the tolerance function, then the method continues in step 90. In step 90, the control system 14 records a point of efficiency speed 92, and stores the point of efficiency speed 92 in the memory device 28. The point of efficiency speed 92 is the treadmill speed 66 that corresponds to the point of efficiency 70 as illustrated in FIG. 2A. The method continues in step 94. In step 94 the treadmill apparatus 12 can be stopped and the subject 18 stops running. The point of efficiency is just a benchmark.

Figure 5:
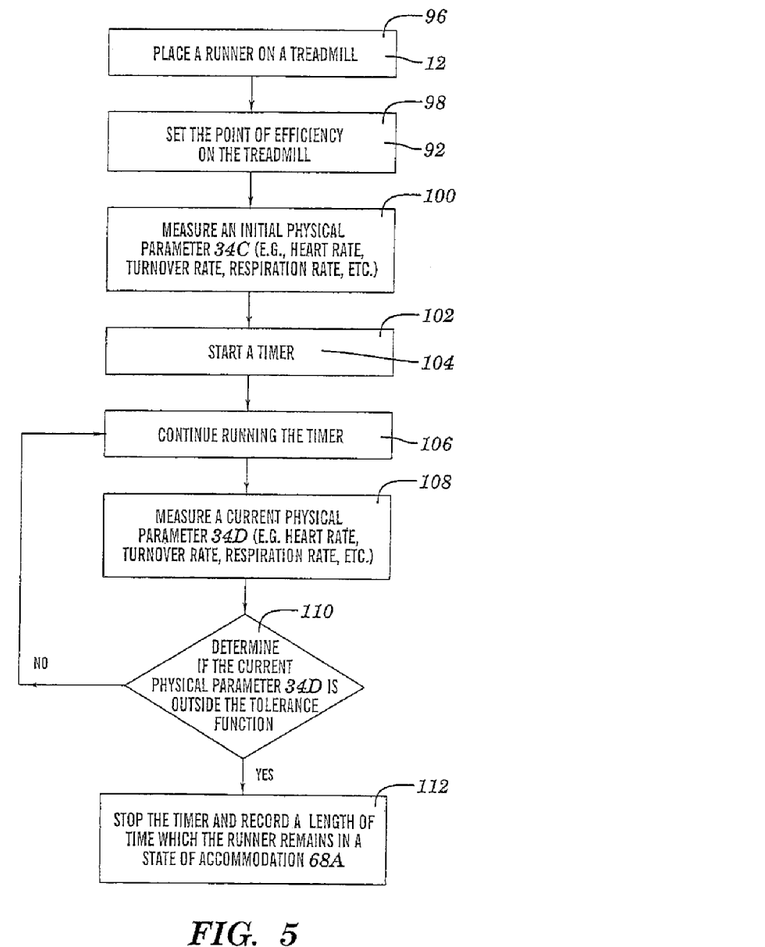
FIG. 5 illustrates a schematic view of determining a length of time which a runner remains in a state of accommodation for a specific embodiment related to running, within the scope of the present invention; and, FIG. 6 illustrates a general diagram of the performance system employed by the method and apparatus, in accordance with the present invention.

FIG. 5 illustrates a schematic view of determining a length of time 74 in which a runner 18 remains in a state of accommodation 68A. In step 96, the runner is placed on the treadmill apparatus 12. In step 98, the treadmill speed 66 is set at, or around, the point of efficiency speed 92 which was determined in step 90 (FIG. 4). In step 100, the control system 14 measures an initial physical parameter 34C. In step 102, the control system 14 starts a timer 104 to measure elapsed time. In step 106, the timer 104 and the treadmill apparatus 12 continue to run. In step 108, a current physical parameter 34D is measured by the control system 14. In step 110, the control system 14 determines if the current physical parameter 34D is outside the tolerance function. The computer 24 of the control system 14 performs this determination by comparing the tolerance function with the current physical parameter 34D. If the current physical parameter 34D is not outside the tolerance function, the method returns to step 106 where the timer 104 continues to run. If the current physical parameter 34D is outside the tolerance function, the method continues in step 112. In step 112, the control system 14 stops the timer 104 and records the length of time "T" in which the subject 18 remained in the state accommodation 68A as illustrated in FIG. 3. Note, again, that inefficiency can be at exhaustion and may be signaled by subject 18.

The subject 18 is further trained by repeating steps 96 through 112 of FIG. 5. Over a period of time, the subject 18 is able to produce a specific level of performance over an improved period of time. As the subject 18 trains and builds up more capacity, the point of efficiency 70A moves to longer and longer lengths of times 74 as illustrated in point of efficiencies 70E, and 70F (FIG. 3). The subject 18 may also be able to run longer in inefficiency and longer overall. This can be tested by using a very "loose", or open-ended tolerance function. Alternatively, the subject 18 can also train and build up more capacity, but due to the particular activity can shorten length of time 74 that the point of efficiency 70A is reached. For example, with weight lifting (e.g., twenty repetitions at a particular weight), the point of efficiency 70A is shortened through the use of the method.

Although the training program for improving performance of the present invention described above describes a method and apparatus for improving human performances in various athletic, running activities, it should be clear to one of ordinary skill in the art that the training program of the present invention is also useful for training and improving performance for other subjects 18 such as animals (e.g., race horses, racing dogs, performance dogs, etc.), viruses, cellular automata, etc. and also improving other physical, emotional, or mental areas.

Another example of an embodiment of the invention would be for the subject 18 to be a human performing mathematical calculations. The mathematical calculations could be, in this embodiment, a person adding mathematical sums. A specific goal could be, for example, the subject 18 is attempting add 100 sums as quickly as possible. The measuring system 10 in this embodiment could be a training machine display the sums to be calculated by the subject 18 one at a time, at a given rate (i.e., analogous to treadmill speed in the running embodiment). The rate of delivering the sums to the subject 18 is increased until the subject 18 cannot answer the sum before the next sum is displayed. By way of example, if the subject's 18 point of efficiency is found to be 1 sum per second and the subject 18 can only answer 10 sums before failure, the subject 18 is trained at that rate. The subject 18 is then trained at that rate so that the subject 18 can increase the total number of sums completed (e.g., 15 sums, 25 sums, 50 sums, etc.). Once, for example, the subject 18 can perform 100 sums at the rate of 1 sum per second, then a new point of efficiency is located. Thus, training would then be conducted at the rate of, for example, 0.75 sums per second.

Similar to the mathematician in the above mentioned embodiment, a weightlifter, for example, would, upon using this method for a period of time, also shorten the time between repetitions (i.e. "reps") of lifting weights. Thus, rather than increasing the amount of weight lifted as a result of training, the weightlifter would be able to shorten the time, both total, and between successive reps of lifting the same amount of weight during training.

Another example of an embodiment of this invention allows for the optimal training of microbes to evolve to be resistant to a hostile environmental factor. The microbial culture (i.e. subject 18) is exposed to increasing levels of a hostile environmental factor until a dramatic change in the die-off of the culture happens. The point of efficiency 70, which is this point, is where the culture will be optimally adaptive. Future generations of the microbial culture are exposed to the environmental factor at the point of efficiency 70 until the culture is substantially unaffected. A new point of efficiency 70 is found by comparing the current effect to an original efficiency graph. The new graph is extended by increasing the amount of the hostile environmental factor until a new point of efficiency 70 is reached. The process is repeated until the culture is no longer adaptive or until the culture reaches a desired level of adaptability.

Another embodiment utilizing the inventive method is for training an adaptive computer program. Similar to the aforementioned bacterial training, the method employed would be to find a resonance point (i.e., the maximum output for a given input) in the system to be trained. The training effect (i.e. output) is maximized for the effort expended by the subject and trainer (i.e., input). The optimal performance can be called the "Raniere Resonance Training Effect™".

The foregoing description of the present invention has been presented for purposes of illustration and description. It is not intended to be exhaustive or to limit the invention to the precise form disclosed, and many modifications and variations are possible in light of the above teaching. For example, the measurement data (e.g, physical parameters 34, speed, time, etc.) may be recorded by any suitable means (e.g., manually, chart, clipboard, etc.). Such modifications and variations that may be apparent to a person skilled in the art are intended to be included within the scope of this invention as defined by the accompanying claims.

I claim:

1. An apparatus comprising:
a performance system, wherein the performance system includes a treadmill;
at least one sensor for measuring a first parameter of a subject, wherein the first parameter is a parameter of a subject being trained and measured by the performance system;
the at least one sensor measuring an initial measurement of the first parameter;
a control system for controlling a second parameter, wherein the second parameter is a speed of the treadmill;
the control system setting an initial value for the second parameter;
the control system determining a range of tolerance surrounding the initial measurement of the first parameter, the range of tolerance being ±2% of a value of the first parameter;
a timer for recording an elapsed time of a given activity;
the control system determining for the given activity, a point of efficiency of the subject by measuring the first parameter of the subject, the point of efficiency being the maximum value of the second parameter whereby a state of accommodation is maintained, the state of accommodation being maintained as long as the subject trains without the value of the first parameter exceeding the range of tolerance, wherein the point of efficiency is determined by repeatedly increasing stress on the subject within the range of tolerance surrounding the initial measurement of the first parameter by controlling the second parameter until just prior to the subject no longer being able to accommodate additional stress and entering a state of inefficiency or exhaustion.

2. The apparatus of claim 1, wherein the control system further comprising a memory device for storing information and data other than the first and second parameters.

3. The apparatus of claim 2, wherein the control system further comprising a display device for displaying the information and data other than the first and second parameters from the memory device.

4. The apparatus of claim 2, wherein the control system further comprising an output port for transmitting information and data other than the first and second parameters from the memory device out to a printer or a remote computer.

5. The apparatus of claim 1, wherein the control system further comprising an input device for allowing an operator to enter commands into the control system.

6. The apparatus of claim 5, wherein the control system wherein the input device is selected from a group consisting of a keyboard, a mouse, a microphone, an optical motion sensor, and a keypad.

7. The apparatus of claim 1, wherein the first parameter is a physical parameter.

8. The apparatus of claim 7, wherein the physical parameter is selected from the group consisting of running turnover rate, stride length, stride strike force, muscle contraction speed, muscle contraction profile, muscle contraction strength, electromagnetic activity profile, chemical activity profile, body temperature, and blood pressure.

9. The apparatus of claim 7, wherein the physical parameter is selected from the group consisting of heart rate, heart beat strength, respiration rate, $VO_2$, perspiration rate, metabolic rate, blood flow, breathing rate, and breath length.

10. The apparatus of claim 8, wherein the performance system further includes a device selected from the group of a computer, a VCR, an auditory device, a visual device, a connection to a transmission system, or combinations thereof.

11. The apparatus of claim 9 wherein the transmission system is selected from the group of internet, intranet, telephone system, acoustic, short wave, satellite, cable TV system, and combinations thereof.

* * * * *